United States Patent [19]
Ethridge

[11] Patent Number: 5,409,490
[45] Date of Patent: Apr. 25, 1995

[54] SHOULDER SEPARATION RECONSTRUCTION

[75] Inventor: J. Kendall Ethridge, Waco, Tex.
[73] Assignee: DePuy Inc., Warsaw, Ind.
[21] Appl. No.: 108,075
[22] Filed: Aug. 16, 1993
[51] Int. Cl.$^6$ .......................... A61B 17/00; A61F 2/32
[52] U.S. Cl. .......................................... 606/80; 606/86; 606/96
[58] Field of Search ........................ 606/80, 86, 87, 88, 606/96, 97, 98, 99, 100, 104

[56] References Cited

U.S. PATENT DOCUMENTS

| | | | |
|---|---|---|---|
| 2,243,717 | 5/1941 | Moreira | 606/104 |
| 2,248,054 | 7/1941 | Becker | 606/104 |
| 2,531,734 | 11/1950 | Hopkins | 606/97 |
| 2,570,465 | 10/1951 | Lundholm | 606/104 |
| 3,892,232 | 7/1975 | Neufeld | 606/104 |
| 4,341,206 | 7/1982 | Perrett | 606/97 |
| 4,959,064 | 9/1990 | Engelhardt . | |
| 4,988,351 | 1/1991 | Paulos | 606/75 |
| 5,071,420 | 12/1991 | Paulos | 606/104 |
| 5,180,388 | 1/1993 | DiCarlo | 606/104 |
| 5,250,055 | 10/1993 | Moore | 606/86 |

OTHER PUBLICATIONS

"Fractures in Adults," J. B. Lippincott Company, vol. 1, pp. 869-910, 1984.

Primary Examiner—Michael A. Brown
Attorney, Agent, or Firm—Barnes & Thornburg

[57] ABSTRACT

A kit for performing surgical reconstruction of a shoulder separation using a device for visualizing the shoulder structure and particularly the clavicle and coracoid process. The kit includes a drill for drilling a hole through the clavicle and the coracoid process. A plurality of guide pins for insertion into the shoulder to define an initial entry position and angle for the drill. The kit also includes a device for reducing the separation between the clavicle and the coracoid process while providing a desired separation therebetween.

25 Claims, 7 Drawing Sheets

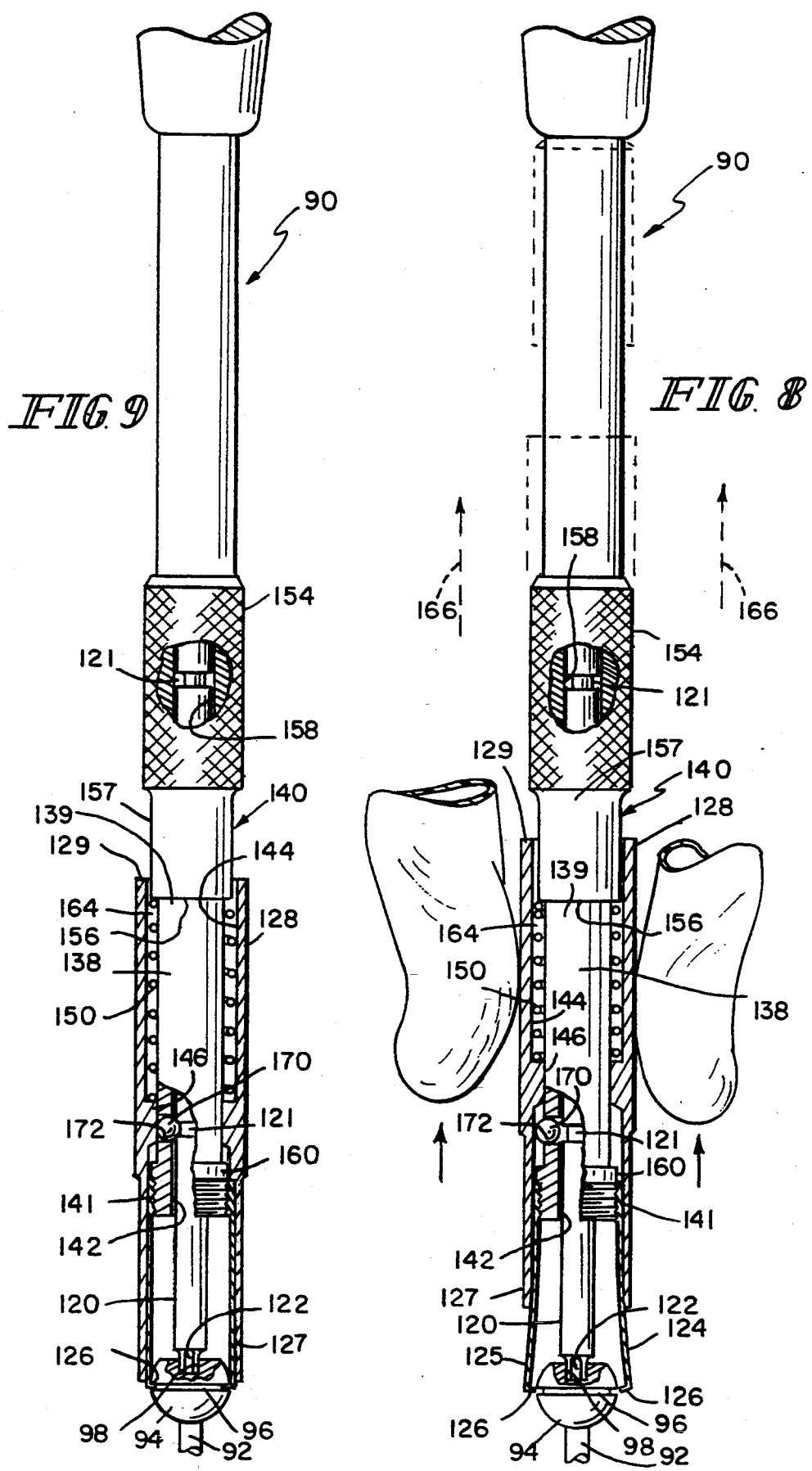

SHOULDER SEPARATION RECONSTRUCTION

BACKGROUND AND SUMMARY OF THE INVENTION

This invention relates to reconstruction surgery and particularly to reconstruction surgery for a type III acromioclavicular separation of the shoulder. More particularly, the invention relates to the use of a percutaneous coracoclavicular screw to reduce the separation between the clavicle and the coracoid process.

Injuries to the acromioclavicular joint are generally classified as type I-V depending on the type and amount of disruption to the acromioclavicular and the coracoclavicular ligaments. A type III acromioclavicular separation of the shoulder is a common injury that occurs primarily from having a fall to the point of the shoulder. A type III injury is characterized by the disruption of the acromioclavicular and coracoclavicular ligaments, the dislocation of the acromioclavicular joint and the upward relative displacement of the clavicle. The coracoclavicular interspace is greater than the normal shoulder, and the deltoid and trapezius muscles are detached from the distal end of the clavicle.

There are presently three treatment options available. Those options are no treatment, closed reduction, and open reduction.

The first treatment option is to do nothing. With such a passive treatment, a decision is made to accept the deformity. Unfortunately, with such passive treatment, the patient must also accept having pain and fatigue after prolonged physical activity or heavy lifting.

The second treatment option available is the closed reduction. Various closed reduction procedures have been tried in the past using straps, casts, and different taping techniques. It has been generally believed that they would all work if they could be applied continuously. Unfortunately, it has been found they do not work because no one can wear them continuously because of skin breakdown and discomfort. As a result, such treatment regimes have rarely been recommended.

The third treatment option available is the open reduction. The open reduction procedure involves a coracoclavicular repair and repair of the ligaments. This procedure corrects the deformity and is generally accepted to give the best results. However, this entails an extensive open operation. The deltoid and trapezius muscles are taken off the clavicle and dissected to expose the underside of the clavicle and the coracoclavicular ligaments and the coracoid. The procedure requires an in-hospital stay, time for healing of the surgical wound, and rehabilitation. The open reduction procedure was generally recommended as the treatment of choice for people who are going to be doing heavy work or active athletics. The remaining population is generally told to accept the deformity and to accept the pain and fatigue after heavy lifting or activity.

Clearly, the passive treatment and the closed reduction treatment options generally provide unacceptable results. The open reduction treatment, while providing generally good results, has the disadvantage of the in-hospital stay plus the extensive time required for healing and rehabilitation. A surgical outpatient technique that would correct the deformity and allow healing of the injury in a normal anatomic position without extensive tissue dissection and less scarring would provide a substantial improvement over current treatment methods.

According to the present invention, a percutaneous method for surgically reconstructing a shoulder separation comprises inserting metal guide pins into the shoulder to bracket the coracoid process. These pins show up as guides in an image producing means such as an X-ray machine with a TV screen showing the image and the pins. Using the guide pins as a guide for a drill, a first hole is drilled in the clavicle and a generally coaxial second hole is drilled in the coracoid process. A screw is inserted through the first hole in the clavicle, and into the second hole in the coracoid process, and the shoulder separation is reduced by screwing the clavicle to the coracoid process.

In preferred embodiments, the step of inserting the metal guide pins comprises the steps of inserting a first pin over the anterior edge of the clavicle and along the medial edge of the coracoid process. A second pin is inserted over the anterior edge of the clavicle and along the lateral edge of the coracoid process, thereby bracketing the coracoid process. A third guide pin is inserted over the posterior edge of the clavicle and to the middle of the coracoid process. When inserted in this fashion, the first, second, and third guide pins define a triangle. The surgeon then uses the center of the triangle as an entry point for the drill and aligns the drill generally parallel to the guide pins. The drilling step also includes overdrilling the first hole in the clavicle to ensure that the first hole diameter is greater than the generally coaxial second hole diameter.

In other preferred embodiments, a kit is provided for performing the surgical reconstruction of a shoulder separation using means for visualizing the shoulder structure and particularly the clavicle and coracoid process. The kit comprises a plurality of guide pins for insertion into the shoulder, means for drilling a hole through the clavicle and the coracoid process, and means for reducing the separation between the clavicle and the coracoid process. In some preferred embodiments, the means for reducing the separation includes a screw having a head and shank wherein the head is generally spherically shaped and formed to include a hexagonal aperture and a circumferential groove. The reducing means also includes a driver that has collet means for engaging the circumferential groove and a hexagonal tip for engaging the hexagonal aperture. The hexagonal tip and collet cooperate with the hexagonal aperture and circumferential groove to rigidly hold the screw on the driver and provide positive directional control of the screw during the reduction treatment. The kit further includes a washer formed to taper into the shape of the head to make removal easier.

By providing pins for targeting the coracoid process, guiding a drill and a percutaneous coracoclavicular screw, and using a means for visualization to assist in obtaining proper positioning and alignment, the present invention advantageously allows the surgeon to correct the deformity without extensive tissue dissection and with less scaring. Furthermore, it allows healing in the normal anatomic position, eliminates the in-hospital stay, and reduces the time required for healing of the surgical wound, and rehabilitation.

Additional objects, features, and advantages of the invention will become apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures in which:

FIG. 8 shows the preferred screwdriver of the present invention in position to engage/disengage a screw; and FIG. 9 shows the same screwdriver positively engaging a screw.

DETAILED DESCRIPTION OF THE DRAWINGS

Figure 1:
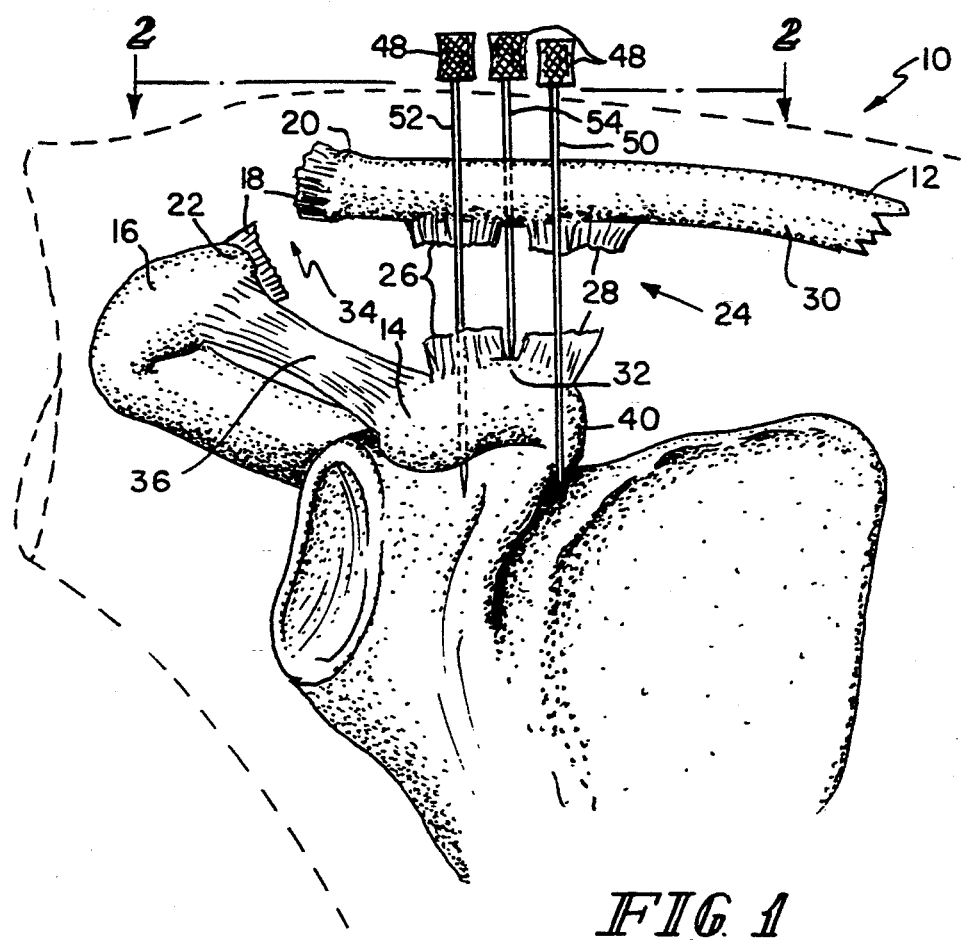
FIG. 1 is an anterior view of a type III acromioclavicular shoulder separation showing three guide pins in place.
Figure 2:
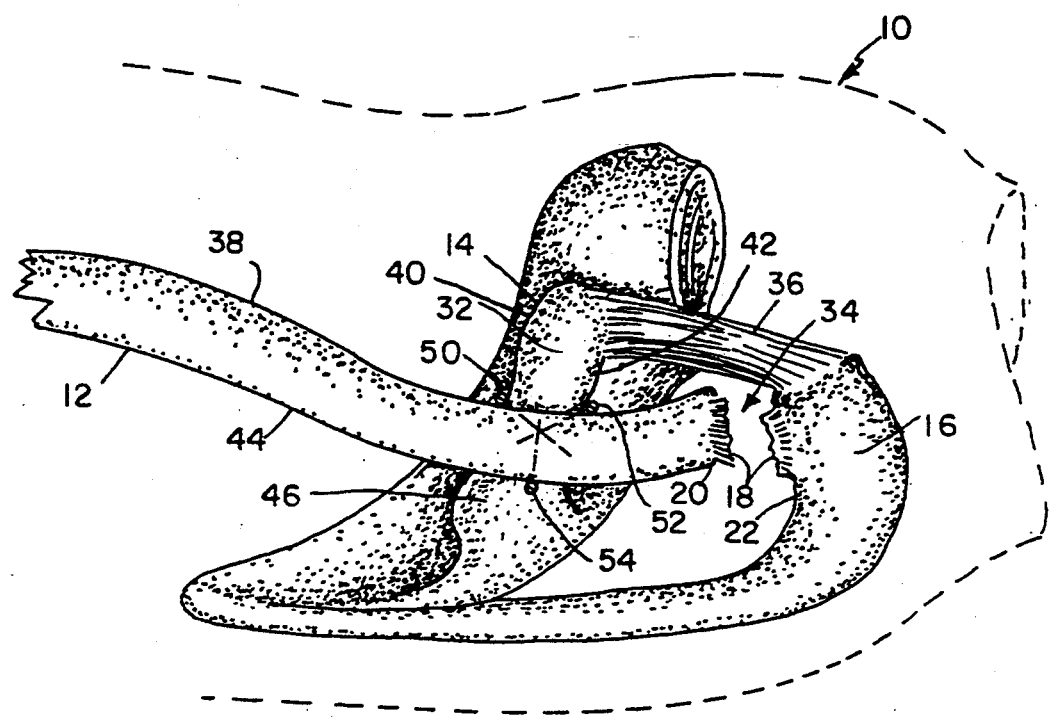
FIG. 2 is a superior view of the shoulder taken along section lines 2—2 of FIG. 1 showing the triangle arrangement of the guide pins.
Figure 3:
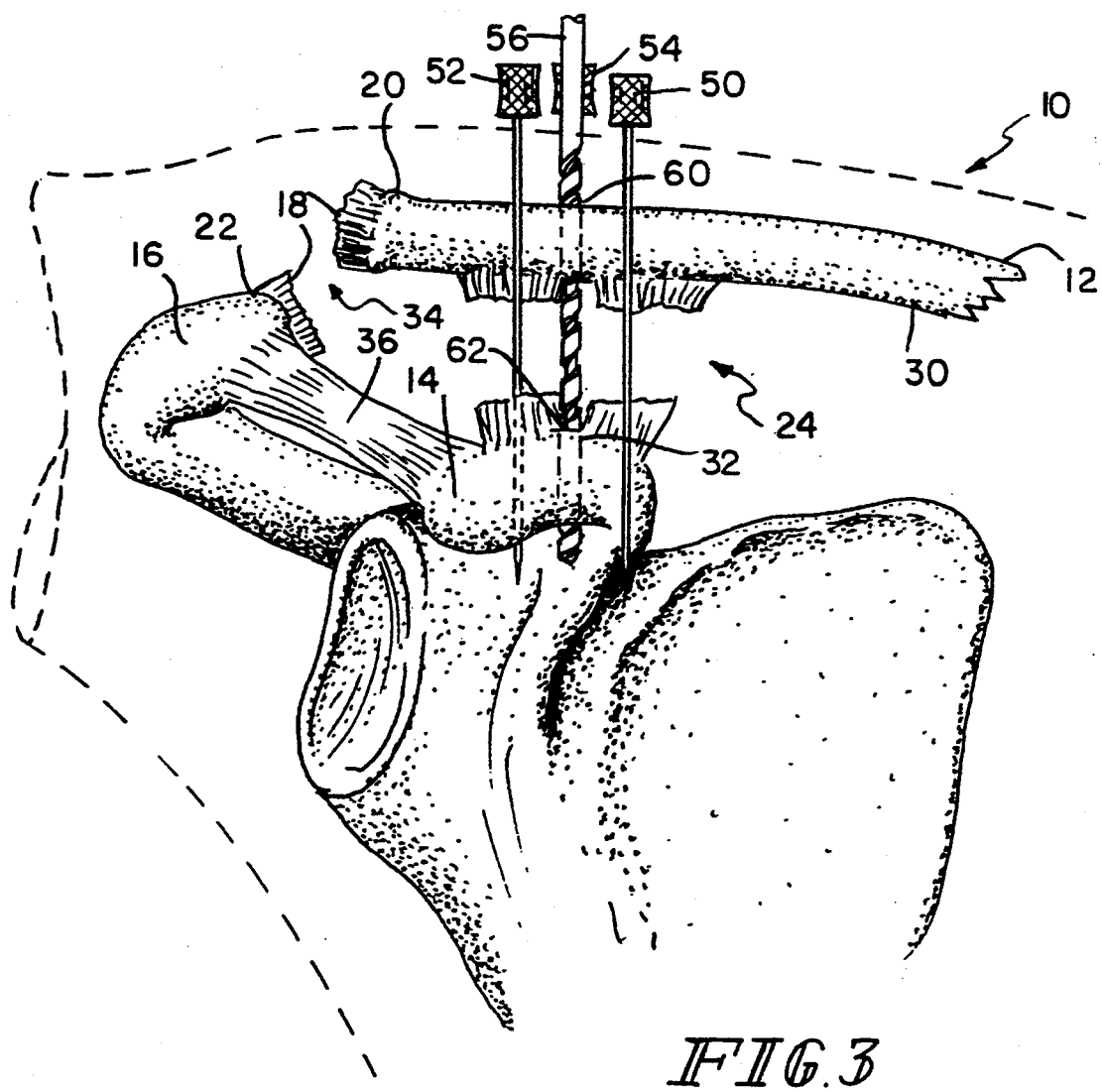
FIG. 3 shows a drill in place between the guide pins and drilling holes in the clavicle and the coracoid process.
Figure 4:
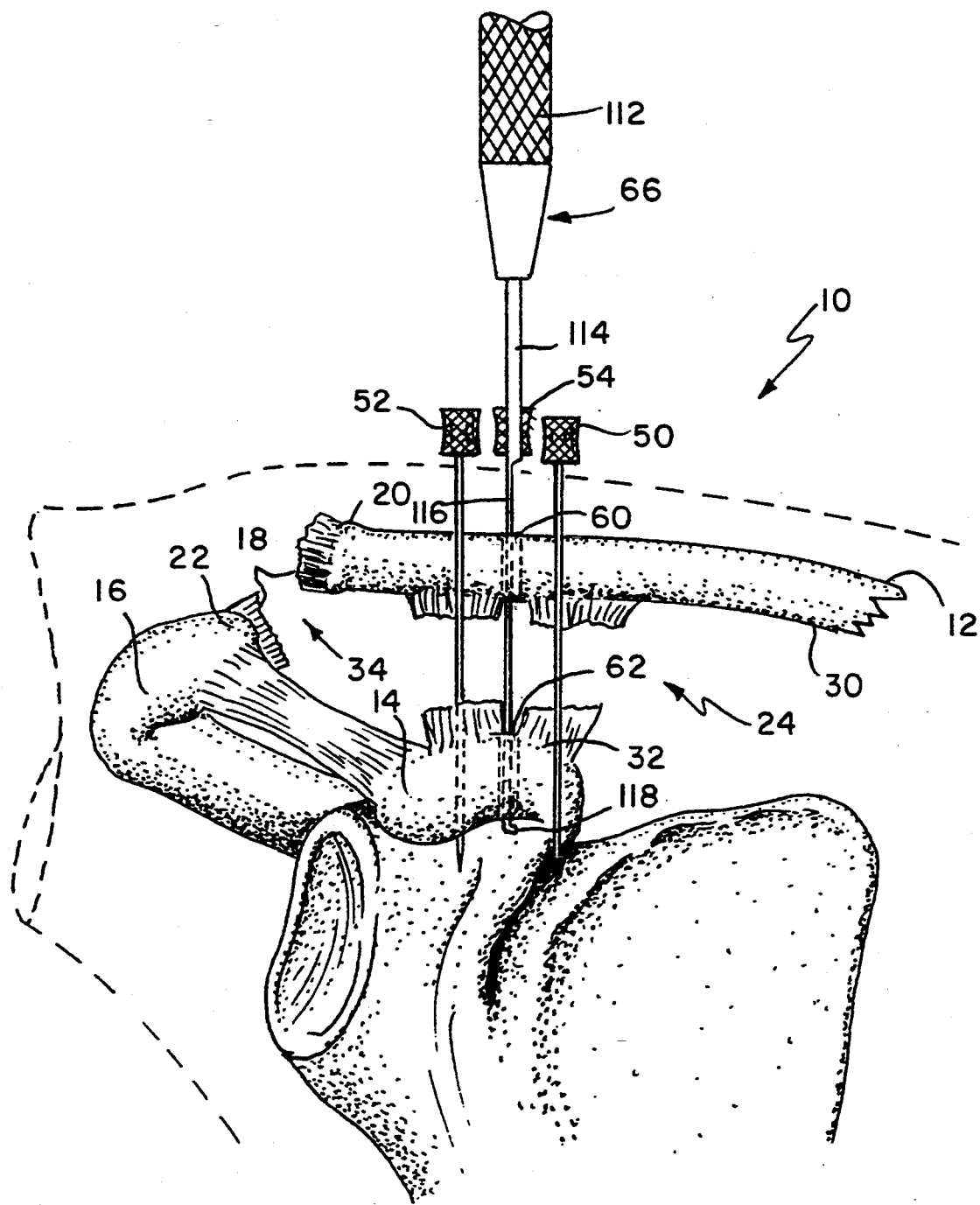
FIG. 4 shows a probe inserted in the holes drilled in the clavicle and the coracoid process 14.
Figure 5:
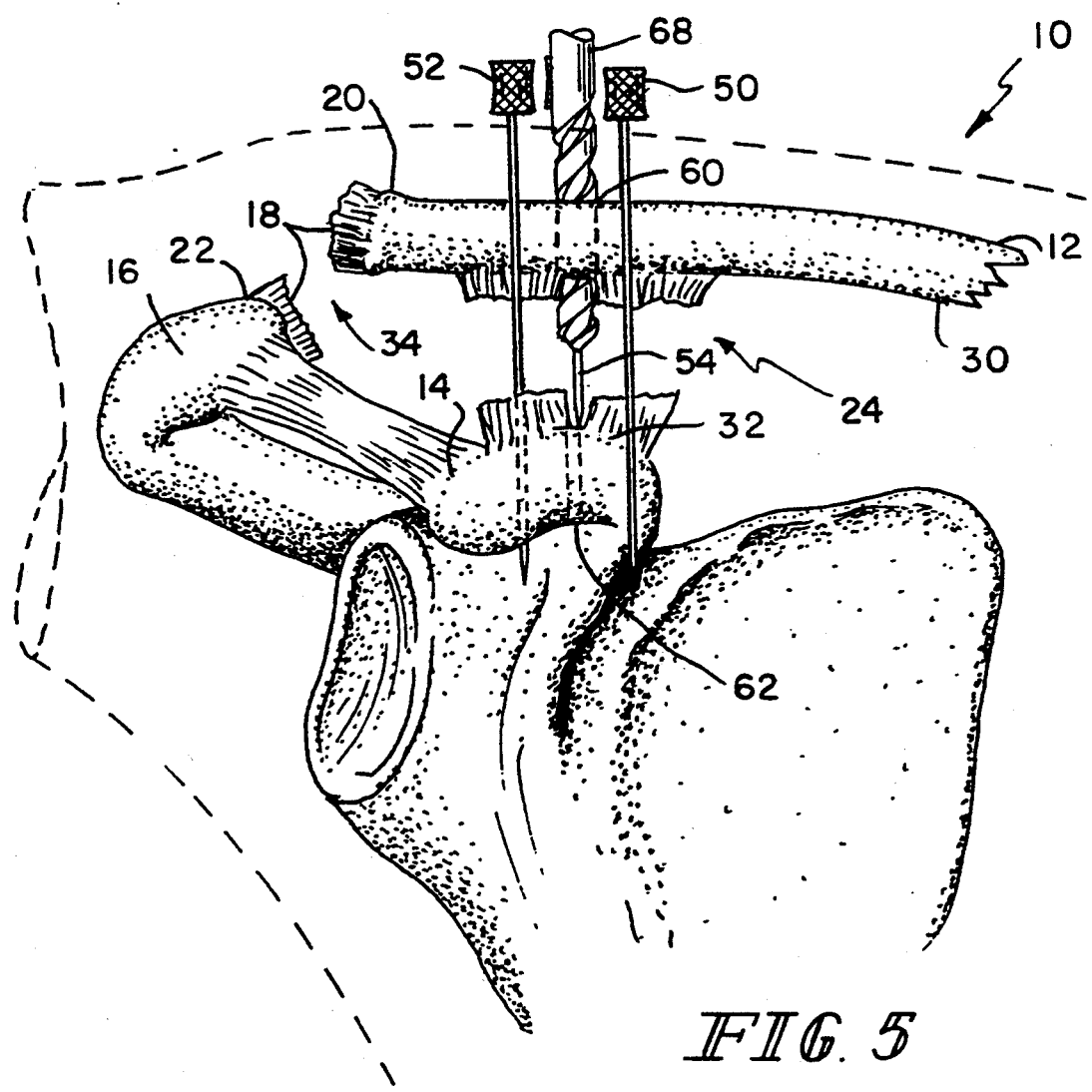
FIG. 5 shows a drill overdrilling the hole in the clavicle.
Figure 6:
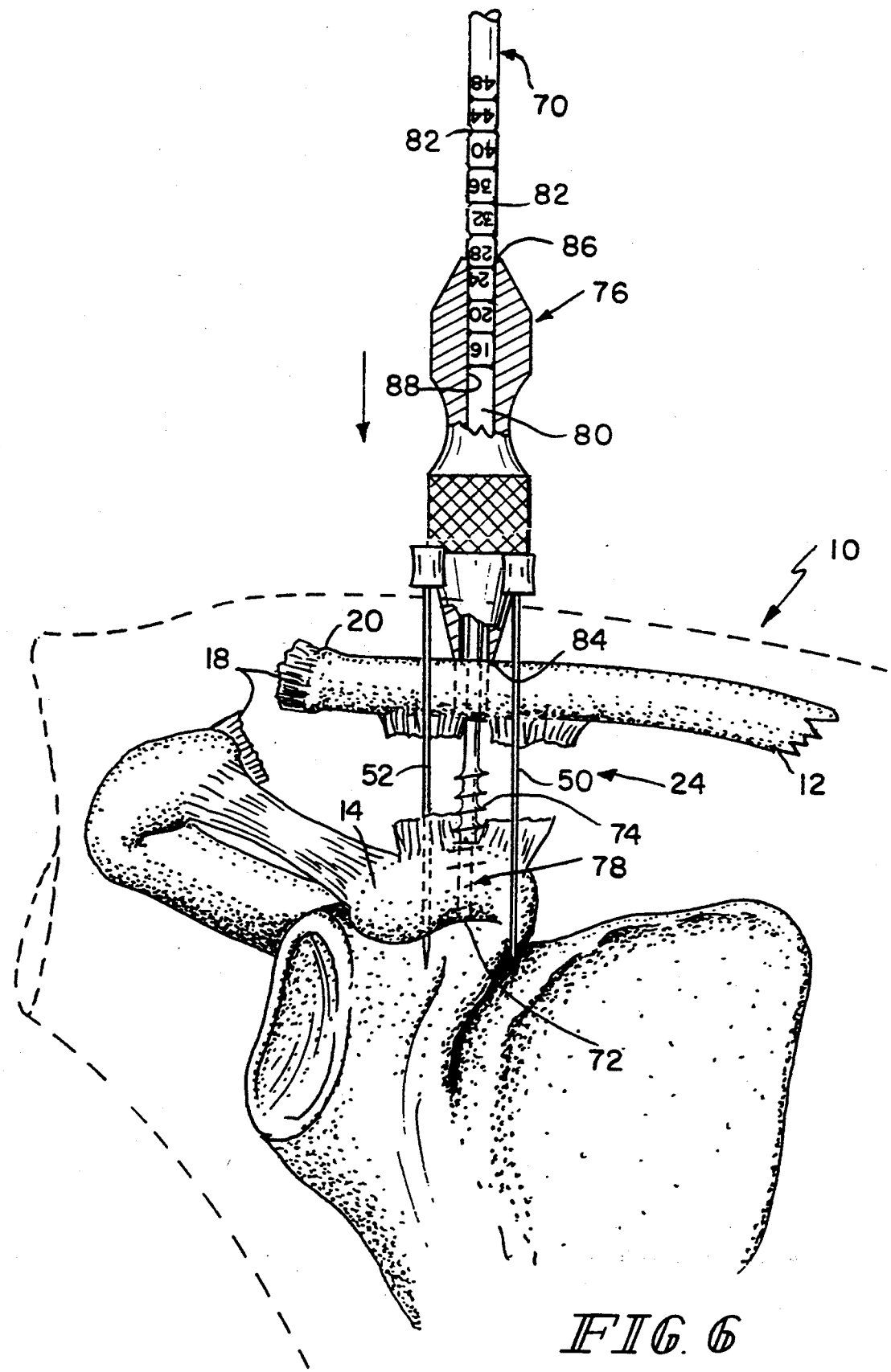
FIG. 6 shows a tap with sleeve for determining screw length drill being inserted through the hole in the clavicle and into the hole in the coracoid process 14.

FIG. 1 and FIGS. 3–7 show an anterior view of a shoulder 10 that has suffered a type III acromioclavical separation injury. FIG. 2 shows a superior view of the shoulder 10.

The structure of the shoulder 10 relevant to a type III separation injury includes the clavicle 12, the coracoid process 14 and the acromion 16. The acromion 16 and the clavicle 12 are connected by the acromioclavicular ligament 18. The acromioclavicular ligament 18 extends from the lateral end 20 of the clavicle 12 to the medial surface 22 of the acromion 16. The coracoid process 14 is connected to the clavicle 12 by the coracoclavicular ligament 24, which comprises the trapezoid ligament 26 and the conoid ligament 28. The coracoclavicular ligament 24 extends from the inferior surface 30 of the clavicle 12 to the superior surface 32 of the coracoid process 14.

A type III acromioclavicular separation is characterized by the disruption of the acromioclavicular and the coracoclavicular ligaments 18, 24, respectively. As shown in FIG. 1 and FIGS. 2–7, the clavicle 12 separates from, and moves away from, the coracoid process 14 and the acromion 16, accompanied by disruption of the coracoclavicular and the acromioclavicular ligaments 18, 24, respectively. The acromioclavicular joint 34 is dislocated and the clavicle 12 is relatively displaced upwardly. The coracoacromial ligament 36 is not impacted in the type III shoulder separation.

Repair of the type III shoulder separation according to the present invention is an out-patient procedure performed with a general anesthetic. The procedure is done with the patient lying flat on a radiolucent table (not shown) using an image intensifier (not shown) to visualize the separation during the reduction procedure and placement of guide pins, drill, and percutaneous screw. The surgery is done with the surgeon standing at the head of the table.

With the patient lying on the radiolucent table (not shown), the acromioclavicular joint 34 is visualized and compared to the normal uninjured acromioclavicular joint (not shown) to determine how much reduction is indicated. The image intensifier can be, for example, an X-ray machine used in conjunction with a TV screen. The picture from the image intensifier should be rotated as necessary to have the clavicle 12 at the bottom of the screen and parallel to the floor, with the right shoulder being to the right of the screen and the left shoulder being to the left of the screen. This makes the surgeon's movements and movements on the screen the same and makes pin and drill placement proprioceptive. By visualizing the uninjured (not shown) and the injured shoulder 10, the uninjured shoulder (not shown) becomes the model for repair.

Figure 7:
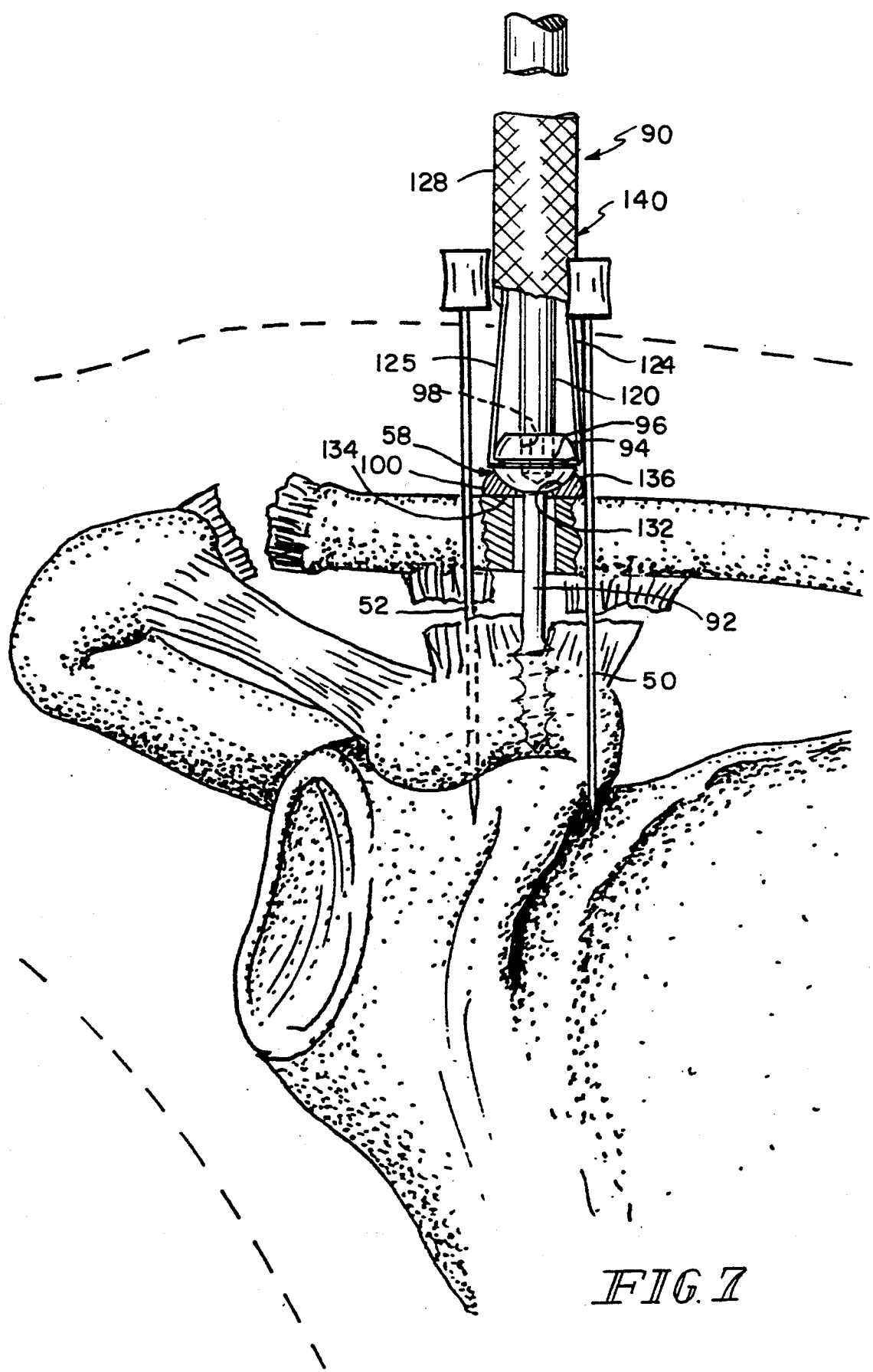
FIG. 7 shows the screw, washer, and driver with collet in place reducing the separation between the clavicle and the coracoid process 14.

Guide pins 50, 52, 54 of various lengths are used to mark the boundaries of the operation area and assist in the proper location and alignment of the drill 56 (FIGS. 3 and 5) and percutaneous screw 58 (FIG. 7). The pins can be any desired length. Preferably they would range from $\frac{3}{4}$″ to $1\frac{3}{4}$″ in length. The preferred pins are approximately 0.045 inches in diameter, having a radiolucent handle 48 at the top. The radiolucent handle 48 can be held with any fingers or pliers, and helps to prevent the pin from passing completely through the skin.

A first guide pin 50 is held in front of the shoulder 10, by hand or with pliers if preferred, so as to project over the clavicle 12 and the coracoid 14 to give a staring reference point for insertion of the first guide pin 50. The image intensifier will show the first guide pin 50 in relation to the clavicle 12 and coracoid process 14. The first guide pin 50 is inserted percutaneously and walked across the clavicle 12 so as to pass adjacent the anterior edge 38 of the clavicle 12, and walked across the coracoid process 14 so as to pass adjacent the medial edge 40 of the coracoid process 14. The term "walked" includes the process of intentionally touching the superior aspect of the clavicle 12 with the pin 50 and moving the pin 50 in small steps along the superior aspect of the clavicle 12 toward the anterior edge 38 of the clavicle 12. This process of moving the pin in small steps ensures the surgeon that the pin is, in fact, adjacent to the clavicle 12. A second guide pin 52 is then held in front of the shoulder 10 and viewed on the image intensifier screen. This allows the second guide pin 52 to be aligned parallel to the first guide pin 50. The second guide pin 52 is then inserted percutaneously and walked across the clavicle 12 so as to pass adjacent the anterior edge 38 of the clavicle 12 and walked across the coracoid process 14 so as to pass adjacent the lateral edge 42 of the coracoid 14. The first and second guide pins 50, 52 should be placed roughly in line with the body and parallel to the floor. A third guide pin 54 is then inserted percutaneously and walked across the clavicle 12 so as to pass adjacent the posterior edge 44 of the clavicle 12 so as to hit the middle of the coracoid 14 posterior to the clavicle 12.

The three guide pins 50, 52, 54 define a triangle, the center of this triangle being the entry point for the drill 56. The drill 56 is held in front of the coracoid 14 over the clavicle 12 to see that it lines up between the first and second guide pins 50, 52, respectively, and overlies the third guide pin 54, as viewed on the image intensifier. The drill 56 is then aligned with, and inserted into, the middle of the clavicle 12. Of course, before the drilling step, the skin and tissue are opened to the clavicle. The surgeon makes a 1 to 1.5 cm (0.39–0.59 inches)

incision axially along the clavicle 12 over the mid portion of the clavicle 12 and sharply dissected to the bone. The drill 56 passes through the clavicle 12 forming a first hole 60 and continues through the top of the coracoid 14 and out the inferior aspect of the coracoid 14, forming a generally coaxial second hole 62.

The drill 56 is removed from the first and second holes 60, 62, respectively, and a probe 66 is passed through the clavicle 12 into the coracoid 14 and out the inferior aspect of coracoid 14. The probe 66 is formed to include a handle 112, a shaft 114 extending from the handle 112 and along the longitudinal axis of the handle 112, and a tip 116. The tip 116, extending from a point on the shaft 114 to the end distal to the handle 112, is formed by removing a portion of the shaft 114 to define a planar surface parallel to the longitudinal axis of the shaft 114. A small distal portion of the tip 116 is bent so as to form a projection 118 extending perpendicular to the longitudinal axis of the tip 116.

The probe 66 is used to ensure that the second hole 62 passes completely through the coracoid 14, passes through the center of the coracoid 14, and is surrounded by solid bone. Once the probe 66 has been inserted through the clavicle 12 into the coracoid 14 and out the inferior aspect of coracoid 14, the probe 66 should be rotated to palpate the inferior aspect of the coracoid 14 in all four quadrants. If the inferior aspect of the hole 62 in the coracoid 14 cannot be palpated in all four quadrants, the guide pins 50, 52, 54 need to be checked for their positioning. If necessary, pins 50, 52, 54 may have to be relocated by aiming slightly more toward the base 46 of the coracoid 14 by aiming down toward the floor. The hole 62 in the coracoid 14 can then be redrilled aiming slightly more posteriorly, thereby moving the hole 62 more toward the base 46 of the coracoid 14.

After the probe 66 is removed, a larger drill 68 is used to overdrill the first hole 60 in the clavicle 12. Enlarging the first hole 60 in this manner renders screw placement easier and reduces bending stresses on the screw 58, thereby decreasing the chance of stress fracture of the screw 58.

A tap 70 is then placed anterior to the shoulder 10 in alignment with the first and second holes 60, 62, respectively. The tap 70 is formed to include a first threaded end 78, a handle (not shown), and a middle portion 80 between the handle (not shown) and the threaded end 78. Gradations 82 are marked on the middle portion 80 of the tap 70. A slide 76, having a first end 84 and a second end 86, is formed to include a central longitudinal bore 88 therein. The bore 78 is sized to allow the middle portion 80 of the tap 70 to fit therein.

When properly aligned with the first and second holes 60, 62, respectively, the tap 70 is passed through the first hole 60 in the clavicle 12 and gently placed in the second hole 62 of the coracoid 14. The threaded end 78 of the tap 70 should enter into the coracoid 14 and threadingly proceed therethrough to form internal threads in the second hole 62 of the coracoid 14. The tap 70 is inserted further as the threads 74 are passed inferior to the coracoid 14. One to three turns of the threads 74 should be provided distal to the coracoid 14. This will ensure that the threads pass completely through the coracoid 14.

With the tap 70 in position, the shoulder separation is manually reduced by pushing the clavicle 12 closer to the coracoid 14. The slide 76 is moved along the middle portion 80 of the tap 70 until the first end 84 comes into contact with the clavicle 12. The gradation 82 thus exposed by the second end 86 of the slide 80 indicates the size of screw 58 to be used to provide the proper reduction of the shoulder separation. Once the proper screw size has been determined, the tap 70 is removed from the shoulder 10. Preferably, a proper sized screw 58 should be mounted on the screw driver 90 prior to removing the tap 70.

The preferred screw 58 includes a threaded shank 92 and a generally ball-shaped head 94. A hexagonal aperture 98 is formed in the head 94 to extend coaxially with the longitudinal axis of the shank 92. A circumferential groove 96 is formed in the head 94 so that it lies in a plane perpendicular to the longitudinal axis of the shank 92.

Preferably, the screw 58 is used in conjunction with a washer 100. The washer 100 has a concave top surface 132 shaped to abut the screw head 94 and a generally flat bottom surface 134 which operably lies adjacent the clavicle 12. The perimetral surface 136 of the washer 100 tapers inwardly from the bottom surface 134 of the washer 100 to the top surface 132. Advantageously, the shape of the washer 100 allows easier removal thereof because tissue doesn't grow over the washer 100 and hold it to the clavicle 12, as happens with conventional flat washers (not shown). Furthermore, the shape of the screw 58 and washer 100 provides a shape 58 that is palpable beneath the skin. Palpability is advantageous because one of the most difficult aspects of removing the screw 58 from the shoulder 10 is initially locating the screw 58 under the skin. Since some patients opt to leave the screw 58 in place, palpability also helps in patient compliance in having the screw removed.

The preferred screwdriver 90 includes a handle (not shown), a shaft 120, a hexagonal tip 122 sized to engage the hexagonal aperture 98 formed in the screw head 94, a plurality of circumferential locking grooves 121 positioned axially along the shaft 120, and a collet assembly 140.

The collet assembly 140 is formed to slide over the shaft 120 and engage the circumferential locking grooves 121 in the shaft 120. The collet assembly 140 comprises a threaded collar portion 141 and a pair of resilient arms 124, 125. A proximal end of each resilient arm 124, 125 is attached to the threaded collar portion 141 so that the arms 124, 125 extend parallel to the longitudinal axis of the collet assembly 140. Fingers 126 are formed at the distal end of each resilient arm 124, 125 so as to extend in the direction perpendicular to the arms 124, 125 and inwardly toward the longitudinal axis of the collet.

The collar portion 141 is screwed onto a locking tube 138 which is formed to include a central bore 142 extending along the length of the locking tube 138. The central bore 142 is sized to slide over the screwdriver shaft 120. The locking tube 138 has a circumferential lip 160 extending radially outwardly therefrom. The lip 160 is axially located to abut the threaded collar 141 when the threaded collar 141 is screwed onto the locking tube 138.

A sliding sleeve 128 is formed to include a central bore 144 extending along the length of the sleeve 128. A shoulder 146 is formed inside the central bore 144 and extends radially inwardly to engage the lip 160 formed on the locking tube 138 when the locking tube 138 is inserted into the sliding sleeve 128. The shoulder 146 is axially located along the central bore 144 of the sliding sleeve 128 to allow the proximal end 127 of the locking sleeve 128 to enclose the collar portion 142 and the arms 124, 125 with the exception of the fingers 126. The sliding sleeve 128 and the locking tube 138 cooperate to define a channel 164 therebetween which extends axially from the shoulder 146 toward the distal end 129 of the sliding sleeve 128.

Spherical locking balls 170 are inserted into apertures 172 formed in the locking tube 138. The apertures 172 are coaxially located with the shoulder 146 when the locking tube 138 is inserted into the central bore 144 of the sliding sleeve 128. The spherical locking balls 170 are sized to be held in engagement with the circumferential locking grooves 121 when the shoulder 146 in the sliding sleeve 128 engages the lip 160 formed on the locking tube 138.

A spring 150 is inserted into the distal end 129 of the sliding sleeve 128 to engage the shoulder 146. The spring 150 is sized to lie in the channel 164.

A screw sleeve 154 is formed to include a threaded aperture 156 which engages threads formed on the distal end 139 of the locking tube 138. When the screw sleeve 154 is threaded onto the locking tube 138, the spring 150 is compressed between the screw sleeve 154 and the shoulder 146 formed in the sliding sleeve 128. The screw sleeve 154 is formed to include a central bore 158 extending along the length thereof to slide over the screwdriver shaft 120. The screw sleeve 154 further includes a proximal portion 157 having a reduced outer diameter. The reduced outer diameter allows the proximal portion 157 to fit into the channel 164, thereby retaining the spring 150 inside the channel 164.

In operation, the spring 150 resiliently pushes the shoulder 146 against the lip 148 formed on the locking tube 128, thereby causing the shoulder 146 to cover the apertures 172 and spherical locking balls positioned therein. As shown in FIG. 8, holding the locking sleeve 154 steady and pulling the sliding sleeve 128 axially in the direction of arrow 166 allows the spherical locking balls 170 to move freely within the apertures 172 to disengage the circumferential locking grooves 121, thereby allowing the entire assembly to move axially along the shaft 120. At the same time, movement of the sliding sleeve 128 uncovers the resilient arms 124, 125 and allows radially outward resilient motion of the arms 124, 125 to allow the fingers 126 to engage/disengage the groove 96 formed on the head 94 of the screw 58.

While the hexagonal tip 122 of the driver 90 engages the hexagonal aperture 98 formed in a screw head 94, the collet assembly 140 can be axially moved along the shaft 120 to position the resilient arms 124, 125 so that fingers 126 are positioned to engage the groove 96 formed in the screw head 94. As shown in FIG. 9, when the fingers 126 are positioned in the groove 96, the screw sleeve 154 is held in place and the sliding sleeve 128 is released. The spring 150 resiliently pushes the sliding sleeve 128 axially away from the screw sleeve 154, causing the spherical locking balls 170 to engage the circumferential locking groove 121 and thereby coupling the collet assembly 140 to the shaft 120. At the same time, the sliding sleeve 128 slides over the resilient arms 124, 125, pushing them radially inwardly to maintain the fingers 126 in the groove 96 formed in the screw head 94.

When the hexagonal tip 122 is engaged in the aperture 98 and the fingers 126 are engaged in the groove 96, screwdriver 90 has positive directional control over the screw 58. The screw can then be inserted through the first hole 60 in the clavical 12 and into the second hole 62 in the coracoid process 14. As the screw 58 is turned, the separation in the shoulder is reduced.

The hexagonal head 122 and the fingers 126 cooperate to rigidly hold the screw 58 and advantageously provide positive directional control over the screw 58. Positive directional control is very important when the screw 58 is being inserted into the second hole 62 in the coracoid process 14 to ensure that the screw 58 is properly aligned with the second hole 62.

More advantageously, the collet assembly 140 can be backed away from the head 94 of the screw 58 leaving the hex drive 122 engaged in the screw 58 for final seating. The ability to retract the collet assembly 140 from the screw 58 before final seating is important as it prevents the collet assembly 140 from obstructing the view on the image intensifier (not shown).

After the tap 70 has been removed, the screw 58 is inserted to pass through the first hole 60 in the clavicle 12 and into the second hole 62 in the coracoid 14. The screw 58 is gently tightened down until the coracoclavicular separation is reduced and the acromioclavicular joint 34 is properly aligned. The appropriate amount of reduction can be determined by visualizing the unaffected shoulder (not shown). If the screw 58 can still be easily turned an additional half turn, it would be desirable to slightly overreduce the shoulder separation to allow for some relaxation due to tissue elasticity.

Although the invention has been described in detail with reference to a certain preferred embodiment, variations and modifications exist within the scope and spirit of the invention as described and defined in the following claims.

I claim:

1. A method for surgically reconstructing a shoulder separation comprising
    inserting metal guide pins into the shoulder to bracket the coracoid process,
    drilling a first hole in the clavicle and a second hole in the coracoid process using the guide pins as a guide for the drill,
    inserting a screw through the first hole and into the second hole, and
    reducing the separation by screwing the clavicle to the coracoid process.

2. The method of claim 1, wherein the step of inserting guide pins includes inserting first and second guide pins to bracket the coracoid process.

3. The method of claim 2, wherein the step of inserting guide pins further includes inserting a third pin to cooperate with the first and second pins to define a triangle.

4. The method of claim 3, wherein the drilling step includes the step of using the center of the triangle as an entry point for a drill.

5. The method of claim 2, wherein the step of inserting guide pins further includes inserting the first pin over the anterior edge of the clavicle and along the medial edge of the coracoid process, inserting the second pin over the anterior edge of the clavicle and along the lateral edge of the coracoid process, and inserting a third guide pin over the posterior edge of the clavicle and to the middle of the coracoid process.

6. The method of claim 2, wherein the drilling step includes aligning the drill generally parallel to the guide pins.

7. The method of claim 2, wherein the drilling step includes overdrilling the first hole in the clavicle to ensure that the first hole diameter is greater than the second hole diameter.

8. A method of surgically reconstructing a shoulder separation comprising arranging means for visualizing the shoulder to visually display the shoulder structure on a screen, obtaining guide pins, which will show on the screen utilizing the visualizing means to determine the proper location of the guide pins, inserting the guide pins into the shoulder to bracket the coracoid process, drilling a first hole in the clavicle and a second hole in the coracoid process using the inserted pins as a guide for the drill, inserting a screw through the first hole and into the second hole, and reducing the separation by screwing the clavicle toward the coracoid process.

9. The method of claim 8, wherein the step of inserting guide pins includes inserting a first pin over the anterior edge of the clavicle and along the medial edge of the coracoid process, inserting a second pin over the anterior edge of the clavicle and along the lateral edge of the coracoid process so as to cooperate with the first pin to bracket the coracoid process, and inserting a third pin over the posterior edge of the clavicle and into the middle of the coracoid process so as to cooperate with the first and second pins to define a triangle.

10. The method of claim 9, wherein the drilling step includes the step of using the center of the triangle as an entry point for the drill.

11. The method of claim 9, wherein the drilling step includes aligning the drill generally parallel to the guide pins.

12. The method of claim 8, wherein the drilling step includes drilling the second hole so that the second hole passes through the coracoid process and exits the inferior aspect of the coracoid process and is generally coaxial with the first hole.

13. The method of claim 8, wherein the drilling step includes overdrilling the first hole in the clavicle to ensure that the first hole diameter is greater than the second hole diameter.

14. A kit for performing surgical reconstruction of a shoulder separation using means for visualizing the shoulder structure and particularly the clavicle and coracoid process, said kit comprising a drill for drilling a hole through the clavicle and the coracoid process, a plurality of guide pins for insertion into the shoulder to define an initial entry position and angle for the drill, and means for reducing the separation between the clavicle and the coracoid process while providing a desired separation therebetween.

15. The kit of claim 14, wherein the plurality of guide pins includes a first pin to be positioned over the anterior edge of the clavicle and along the medial edge of the coracoid process, a second pin to be positioned over the anterior edge of the clavicle and along the lateral edge of the coracoid process, and a third pin to be positioned over the posterior edge of the clavicle and into the middle of the coracoid process.

16. The kit of claim 14, wherein the reducing means includes a screw to be inserted through the hole in the clavicle and into the hole in the coracoid process.

17. The kit of claim 16, wherein the screw is formed to include a shank and a washer to be coupled thereto and a generally spherically shaped head having means for retaining a driver.

18. The kit of claim 17, wherein the washer includes a bottom surface, a generally concave top surface that conformingly abuts the generally spherically shaped head and a perimetral surface extending between the top and bottom surfaces that converges from the bottom surface to the top surface.

19. The kit of claim 17, wherein the means for retaining includes a circumferential groove formed on the screw head and collet means for engaging the circumferential groove, the collet means being formed on the driver.

20. The kit of claim 14, wherein the reducing means includes a driver and a screw having means for retaining the driver.

21. The kit of claim 20, wherein the means for retaining includes a circumferential groove around the head of the screw and collet means for holding the screw, the collet means being formed on the driver to engage the circumferential groove.

22. The kit of claim 14, further comprising probe means for palpating the hole in the coracoid process to determine that the hole is properly located.

23. The kit of claim 14, further comprising means for forming internal threads in the hole in the coracoid process.

24. The kit of claim 23, wherein the forming means includes a tap having a shaft and a slide member that slidingly engages the shaft.

25. The kit of claim 24, wherein the shaft is formed to include gradations indicative of screw size and the slide member is operably positioned to indicate a preferred screw size.

* * * * *